United States Patent
Shkumat et al.

(10) Patent No.: US 8,019,044 B2
(45) Date of Patent: Sep. 13, 2011

(54) IMAGE ACQUISITION FOR DUAL ENERGY IMAGING

(76) Inventors: Nick A. Shkumat, Houston, TX (US);
Jeffrey H. Siewerdsen, Toronto (CA);
John Yorkston, Penfield, NY (US);
Richard L. Van Metter, Washington, DC (US)

( * ) Notice: Subject to any disclaimer, the term of this patent is extended or adjusted under 35 U.S.C. 154(b) by 147 days.

(21) Appl. No.: 12/370,893

(22) Filed: Feb. 13, 2009

(65) Prior Publication Data
US 2009/0207966 A1 Aug. 20, 2009

Related U.S. Application Data

(60) Provisional application No. 61/028,950, filed on Feb. 15, 2008.

(51) Int. Cl.
*H05G 1/32* (2006.01)
*H05G 1/64* (2006.01)
*G21K 3/00* (2006.01)
*G01N 23/087* (2006.01)

(52) U.S. Cl. .......... 378/98.9; 378/53; 378/156; 378/158
(58) Field of Classification Search ............ 378/5, 16, 378/53, 98.9, 98.11, 156, 158
See application file for complete search history.

(56) References Cited

U.S. PATENT DOCUMENTS

| | | | | |
|---|---|---|---|---|
| 4,445,226 | A * | 4/1984 | Brody | 378/98.9 |
| 4,559,557 | A * | 12/1985 | Keyes et al. | 378/98.11 |
| 4,686,695 | A * | 8/1987 | Macovski | 378/146 |
| 6,285,740 | B1 * | 9/2001 | Seely et al. | 378/98.9 |
| 6,683,934 | B1 * | 1/2004 | Zhao et al. | 378/9 |
| 6,950,492 | B2 * | 9/2005 | Besson | 378/5 |
| 7,372,943 | B2 * | 5/2008 | Bernhardt | 378/98.12 |
| 7,742,568 | B2 * | 6/2010 | Smith | 378/98.11 |
| 7,746,976 | B2 * | 6/2010 | Huo et al. | 378/54 |

OTHER PUBLICATIONS

N. A. Shkumat et al., "Imaging Performance and Acquisition Technique for a New Dual-Energy Imaging System", Ontario Cancer Institute, Princess Margaret Hospital, University Health Network. AAPM (The American Association of Physicists in Medicine) Annual Meeting, Orlando, Florida, Jul. 2006.
N.A. Shkumat et al., "Optimization of Image Acquisition Techniques for Dual-Energy Imaging of the Chest", Med. Phys. 34 (10), Oct. 2007, 2007 Am. Assoc. Phys. Med., pp. 3904-3915.
N.A. Shkumat et al., "Development and Implementation of a High-Performance, Cardia-Gated Dual-Energy Imaging System", Medical Imaging, 2007: Physics of Medical Imaging, Proc. of SPIE vol. 6510, 651006, (2007).
N.A. Shkumat, WE-E-330D-05, "Investigation of Imaging Performance and Acquisition Technique for a New Dual-Energy Chest Imaging System", Abstract, Medical Physics, vol. 33, No. 6, Jun. 2006, pp. 2252.

* cited by examiner

*Primary Examiner* — Allen C. Ho (57) ABSTRACT

Acquisition techniques for dual energy (DE) chest imaging system. Technique factors include the added x-ray filtration, kVp pair, and the allocation of dose between low- and high-energy projections, with total dose equal to or less than that of a conventional chest radiograph. Factors are described which maximize lung nodule detectability as characterized by the signal difference to noise ratio (SDNR) in DE chest images. kVp pair and dose allocation are described using a chest phantom presenting simulated lung nodules and ribs for thin, average, and thick body habitus. Low- and high-energy techniques ranged from 60-90 kVp and 120-150 kVp, respectively, with peak soft-tissue SDNR achieved at [60/120] kVp for patient thicknesses and levels of imaging dose. A strong dependence on the kVp of the low-energy projection was observed.

4 Claims, 9 Drawing Sheets

IMAGE ACQUISITION FOR DUAL ENERGY IMAGING

CROSS REFERENCE TO RELATED APPLICATIONS

Reference is made to, and priority is claimed from, commonly assigned application U.S. Ser. No. 61/028,950, entitled OPTIMIZAION OF IMAGE ACQUISITION TECHNIQUE FOR DUAL-ENERGY IMAGING OF THE CHEST, and filed on Feb. 15, 2008 in the name of Van Metter, incorporated herein by reference.

FIELD OF THE INVENTION

The invention relates generally to the field of dual energy projection radiography, and in particular to dual energy imaging of the chest.

BACKGROUND OF THE INVENTION

In multiple-energy projection radiographic imaging, a number of images of the same object are acquired that reveal the x-ray transmittance of the object for differing x-ray spectra. In dual energy imaging, two images of the same object are acquired sequentially under different x-ray beam conditions, such as beam energy and filtration. These images are proportional to the x-ray transmittance of the object for the differing x-ray spectra. These images can then be decomposed to produce material specific images, such as soft-tissue and bone images. Radiographic imaging procedures that require multiple exposures, such as dual energy imaging, may acquire multiple images over a period of time.

Lung cancer presents an burden to society because survival is low for advanced stage disease. The key to survival is early detection. Conventional chest radiography has proven inadequate in the detection of early-stage disease, missing 50% of nodules measuring 10 mm or less. The lack of sensitivity is attributed in large part to the superposition of anatomical structures in the projection image, i.e., the obscuration of subtle soft-tissue nodules by overlying "anatomical noise," such as the ribs and clavicles. Low-dose CT (LDCT) offers some improvement in diagnostic sensitivity; however, diagnostic specificity (as well as increased cost and radiation dose) presents a remaining challenge.

Dual-energy (DE) imaging has been investigated for detection of lung disease.

Conventionally, DE imaging has been limited by clinical implementation, a relatively high radiation dose, and the lack of a high-performance detector. The availability of digital detectors (also referred to as flat-panel detectors (FPDs)) offering real-time digital readout and performance consistent with the demands of chest radiography, however, promises to remove conventional limitations, permitting high-performance DE imaging at total dose equivalent to that of a single chest radiograph. Further, such renewed interest in DE imaging using FPDs extends beyond chest imaging to include real-time DE fluoroscopy (e.g., vascular and cardiac interventions) and DE computed tomography. In each case, it is desired to maximizing DE imaging performance.

The present invention describes the DE image acquisition techniques for a chest imaging system. Factors are described for dual-energy filtration, kVp-pair, and allocation of dose between low- and high-kVp projections. It is desired to maximize soft-tissue visibility of lung nodules in DE soft-tissue images.

SUMMARY OF THE INVENTION

Any objects provided are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided an x-ray imaging system for generating multiple energy x-ray images. The system includes an image detector, a filter, and a computer. The image detector is spaced from an x-ray source wherein the space accommodates a subject to be imaged. The x-ray source is selectively switchable between first and second different x-ray energy levels, wherein the first x-ray energy level is selected within a range of approximately 50-70 kVp and the second x-ray energy level is selected within a range of approximately 110-130 kVp. A dose allocation is selected within a range of approximately 30-40 percent. The filter is disposed between the x-ray source and the subject. The filter is selected of a filter material range $Z_{filter}$ of approximately 25-50 and a thickness range of approximately 0.3-3 mm. The computer controls the x-ray detector to irradiate the subject with the first and second energy levels to generate first and second x-ray images.

In one particular arrangement of the x-ray imaging system, the first x-ray energy level is approximately 60 kVp; the second x-ray energy level is approximately 120 kVp; the dose allocation is approximately 30 percent; and the filter having a filter material range $Z_{filter}$ of approximately 47 and a thickness of approximately 0.4-0.5 mm.

According to another aspect of the invention, there is provided a method acquiring dual energy x-ray images. The method includes providing a computer to control the acquisition of first and second x-ray images of a subject using an x-ray detector and an x-ray source to irradiate the subject. A filter is positioned between the x-ray source and the subject during the acquisition of the first and second images of the subject, the filter being selected of a filter material range $Z_{filter}$ of approximately 25-50 and a thickness range of approximately 0.3-3 mm. The first x-ray image of the subject is generated at a first energy level, wherein the first energy level is selected within a range of approximately 50-70 kVp. The second x-ray image of the subject is generated at a second energy level, wherein the second energy level is selected within a range of approximately 110-130 kVp, with a dose allocation being selected within a range of approximately 30-40 percent.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

The following is a detailed description of the preferred embodiments of the invention, reference being made to the drawings in which the same reference numerals identify the same elements of structure in each of the several figures.

Figure 1:
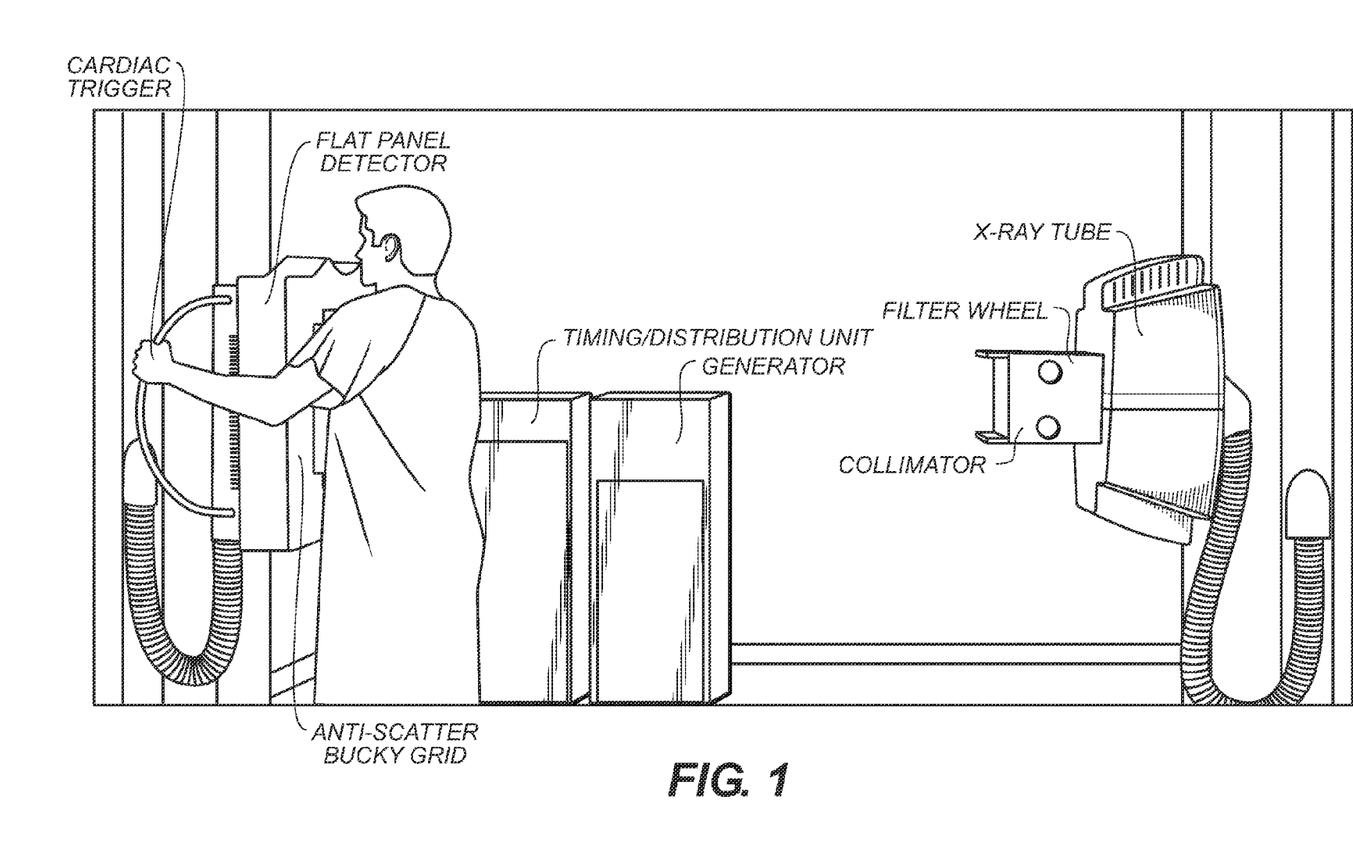
FIG. 1 shows an exemplary dual energy (DE) imaging system in accordance with the present invention.

An exemplary dual energy (DE) imaging system is illustrated in FIG. 1. The system is based on a radiographic chest stand (RVG 5100 system, Eastman Kodak Company, Rochester, N.Y.), modified to perform cardiac-gated DE imaging.

The system includes a high-frequency, 3-phase generator (VZW 293ORD3-03, CPI, Georgetown, Ontario), a 400 kHU x-ray tube (Varian Rad-60, Salt Lake City, Utah), and a 10:1 antiscatter Bucky grid (Advanced Instrument Development Inc., Melrose Park, N.J.). Modifications to the RVG 5100 platform include:

1.) a collimator (Ralco R302 ACS/A, Biassono, Italy) incorporating a computer-controlled filter-wheel;

2.) a high-performance flat-panel detector, FPD (Trixell Pixium-4600, Moirans, France);

3.) a cardiac gating system based on a fingertip pulse oximeter (Nonin Ipod, Plymouth, Minn.); and 4.) the associated image acquisition and processing/display workstations.

The filter wheel supports four positions for differential filtration of low- and high-kVp beams. The added filtration for DE imaging is described in detail below, suggesting low-kVp filtration equivalent to 2.5 mm Al (equal to the inherent filtration of the x-ray tube and collimator) and high-kVp filtration by an additional 2 mm Al+0.6 mm Ag.

The added filtration in the two remaining filter wheel positions is used for conventional DR image acquisition (1 mm Al+0.2 mm Cu) and quality assurance tests (2 mm Al). The Pixium-4600 is a large-area (~43×43 cm$^2$) indirect-detection (250 mg/cm2 CsI:Tl) FPD composed of 3121×3121 pixels (143 μm pitch) with a 68% fill-factor based on a double-diode pixel architecture. To minimize misregistration associated with cardiac motion between low- and high-kVp projections, a cardiac gating system triggers x-ray exposure within the quiescent phase of the heart cycle.

DE soft-tissue and bone-only images ($I_{soft}^{DE}$ and $I_{bone}^{DE}$, respectively) were decomposed by weighted log-subtraction:

$$\ln(I_{soft}^{DE}) = \ln(I^H) - w_s \ln(I^L) \tag{1a}$$

$$\ln(I_{bone}^{DE}) = -\ln(I^H) + w_b \ln(I^L) \tag{1b}$$

where $I^L$ represents the low-energy image, $I^H$ the high-energy image, and $w_s$ and $w_b$ are cancellation parameters for bone and soft tissue, respectively. Weighted log-subtraction was employed because of its applicability to cascaded systems modeling and computational simplicity, with cancellation parameters chosen either theoretically (from the ratio of attenuation coefficient at low- and high-kVp) or experimentally (iteratively selected to minimize contrast of the material to be canceled).

Radiation dose was quantified below in terms of the imparted energy:

$$\varepsilon = \int_0^E q_E(E) \cdot \eta(E; t) \, dE \tag{2}$$

where $\varepsilon$ has units of μJ/cm$^2$, $q_E(E)$ is the incident x-ray energy fluence, and $\eta(E; t)$ is the fraction of energy absorbed as a function of x-ray energy, E, and patient (water) thickness, t. The imparted energy associated with typical DR chest imaging was determined by computing x-ray spectra for typical clinical techniques (kVp, mAs, source-to-patient distance, and filtration) integrated with water thicknesses that approximated patient chest habitus. Throughout, the total imparted energy for a DE acquisition was equal to or less than that of a single DR radiograph.

For comparison, the entrance surface dose (ESD) was computed using the f-factor ($\overline{f_{water}}$) and backscatter fraction ($\overline{BSF}$) averaged over the incident x-ray spectrum:

$$ESD = \left[ \int_0^E \frac{q_o(E)}{(q/X)(E)} dE \right] \overline{BSF} \cdot \overline{f_{water}} \tag{3}$$

where ESD has units of mGy, $q_o(E)$ is the incident x-ray spectrum (computed using the spektr implementation of the TASMIP algorithm), and $(q/X)(E)$ is the fluence per unit exposure.

A particular factor in DE imaging is the proportion of total dose imparted by the low- and high-kVp projections, referred to as dose allocation. For a fixed total imparted energy, $\varepsilon^{total}$, the dose allocation, $A_\varepsilon$, is:

$$A_\varepsilon = \frac{\varepsilon^L}{\varepsilon^L + \varepsilon^H} \tag{4}$$

where $\varepsilon^L$ and $\varepsilon^H$ are the energies imparted in low- and high-kVp projections, respectively. Dose allocation ranges from 0 (all dose allocated to the high-kVp projection) to 1 (all dose allocated to the low-kVp projection).

With regard to the Dual-energy image signal, a metric used to characterize DE imaging performance in the visualization of soft-tissue structures is the signal—difference—to noise ratio (SDNR$^{DE}$) in a lung nodule relative to background (lung). For the soft-tissue image, henceforth denoted I$^{DE}$, the signal in the DE image may be written:

$$I^{DE} = \frac{I^H}{(I^L)^{w_s}} \tag{5}$$

The relative signal difference between the nodule and background can be measured as the difference in mean signal between the two regions, normalized by the mean signal level:

$$SD_{rel}^{DE} = \frac{\overline{I_{nodule}^{DE}} - \overline{I_{background}^{DE}}}{\overline{I_{mean}^{DE}}} \tag{6}$$

where $\overline{I_{nodule}^{DE}}$ and $\overline{I_{background}^{DE}}$ are the mean signal in nodule and background regions of a DE image, respectively, and the mean signal is simply:

$$I_{mean}^{DE} = \tfrac{1}{2}(\overline{I_{nodule}^{DE}} + \overline{I_{background}^{DE}})$$

Signal difference is used as a measure of contrast.

Cascaded systems analysis provides an analytical description of signal and noise propagation in an imaging system and has been applied successfully to several imaging systems to compute the DE signal and noise across a broad range of energy, dose, filtration, etc. The detector signal in either the low- or high-energy image is proportional to the linear combination of gain factors associated with the imaging chain:

$$I = X\left(\frac{\overline{q_0}}{X}\right) a_{pix}^2 \overline{g_1 g_2 g_4} \tag{8}$$

where detector signal, I, has units of electrons per pixel. X-ray spectra were computed using spektr, X is the exposure at the detector, and $a^2_{pix}$ is the sensitive area of the pixel aperture. The gain parameters, $\overline{g_1}$ (quantum detection efficiency), $\overline{g_2}$ (scintillator gain), and $\overline{g_4}$ (coupling efficiency of secondary quanta) were computed as described previously.

With regard to Dual-energy image noise, noise in DE images can be measured in terms of the variation in pixel values in regions of the nodule and background, with relative noise given by the mean standard deviation divided by the mean signal:

$$\sigma_{rel}^{DE} = \frac{1/2(\sigma_{nodule}^{DE} + \sigma_{background}^{DE})}{I_{mean}^{DE}} \tag{9}$$

where $\sigma_{nodule}^{DE}$ and $\sigma_{background}^{DE}$ are the standard deviations in signal level in nodule and background.

Theoretically, the noise in DE images is computed using the noise-power spectrum (NPS) for the low- and high-kVp projections, combined to yield the dual-energy NPS as:[34]

$$NPS_{rel}^{DE} = NPS_{rel}^{H} + w_s^2 NPS_{rel}^{L} \tag{10}$$

The NPS was computed using again cascaded systems analysis, including effects such as K-fluorescent x-rays, scintillator blur, noise aliasing, and electronic noise. The pixel variance was computed by integrating the NPS over the Nyquist region of the 2D Fourier domain, yielding the relative DE pixel noise:

$$(\sigma_{rel}^{DE})^2 = (\sigma_{rel}^{H})^2 + w_s^2 (\sigma_{rel}^{L})^2 \tag{11}$$

where $(\sigma_{rel}^{H})^2$ and $(\sigma_{rel}^{L})^2$ are the relative variances in high- and low-kVp images, respectively, and $w_s$ is the weighting parameter for bone cancellation calculated from the ratio of the effective low- and high-kVp linear attenuation coefficients:

$$w_s = \frac{\overline{\mu}_{bone}^{H} x_{bone}}{\overline{\mu}_{bone}^{L} x_{bone}} = \frac{\overline{\mu}_{bone}^{H}}{\overline{\mu}_{bone}^{L}} \tag{12}$$

$$= \frac{\ln(I_{bone}^{H}/I_{bone,0}^{H})}{\ln(I_{bone}^{L}/I_{bone,0}^{L})} \tag{13}$$

where $I_{bone,0}$ denotes the signal without bone attenuation.

With regard to Dual-energy image SDNR, the SDNR is measured in DE images of a chest phantom as the ratio of relative signal difference and noise [Eqs. (6) and (9), respectively]:

$$SDNR^{DE} = \frac{SD_{rel}^{DE}}{\sigma_{rel}^{DE}} \tag{14}$$

Similarly for theoretical calculations, $SDNR^{DE}$ is computed as the ratio of relative signal difference and noise as computed by cascaded systems analysis [Eqs. (5), (8), (10), and (11)].

The effect of differential added filtration between low- and high-kVp projections has been examined as a function of the material type (atomic number, $Z_{filter}$) and thickness ($s_{filter}$) of added filtration. Performance has been evaluated in terms of SDNR as well as dose and tube loading characteristics. The contrast between nodule and lung in a DE image is calculated from the difference in attenuation coefficients at low- and high-kVp:

$$C^{DE} = \left[(\mu_{nodule}^{H} - \mu_{lung}^{H}) - \frac{\mu_{bone}^{H}}{\mu_{bone}^{L}}(\mu_{nodule}^{L} - \mu_{lung}^{L})\right] d_{nodule} \tag{15}$$

where μ is the effective attenuation coefficient for nodule, lung, or bone averaged over the low- or high-kVp spectra,[33] and $d_{nodule}$ is the thickness of the nodule. This equation indicates that increasing the spectral separation improves nodule contrast, accomplished by hardening the high-kVp beam or softening the low-kVp beam (e.g., with a K-edge filter). Some studies indicate that effects of the low-kVp filter (e.g., softening the beam with a ~0.1-0.2 mm Ce) are fairly small because of hardening of the beam by the patient. The results below relate to the high-kVp filter, keeping the low-kVp filter fixed at 2.5 mm Al (equal to the inherent filtration of the tube and collimator).

Calculations have been performed on the basis of a simulated chest phantom composed of 10 cm water and 10 cm inflated lung. Ribs were approximated as 5 mm cortical bone, and pulmonary nodules as 9.5 mm polyethylene. The signal difference, noise, and SDNR in DE images were calculated as in Sec. II. B 3 as a function of the atomic number ($Z_{filter}$=1-92) and thickness ($s_{filter}$=0-2.5 mg/cm²) of added filtration. The exposure at the detector was taken to be 1 mR, and patient dose was calculated in terms of the imparted energy.

Figure 2A:
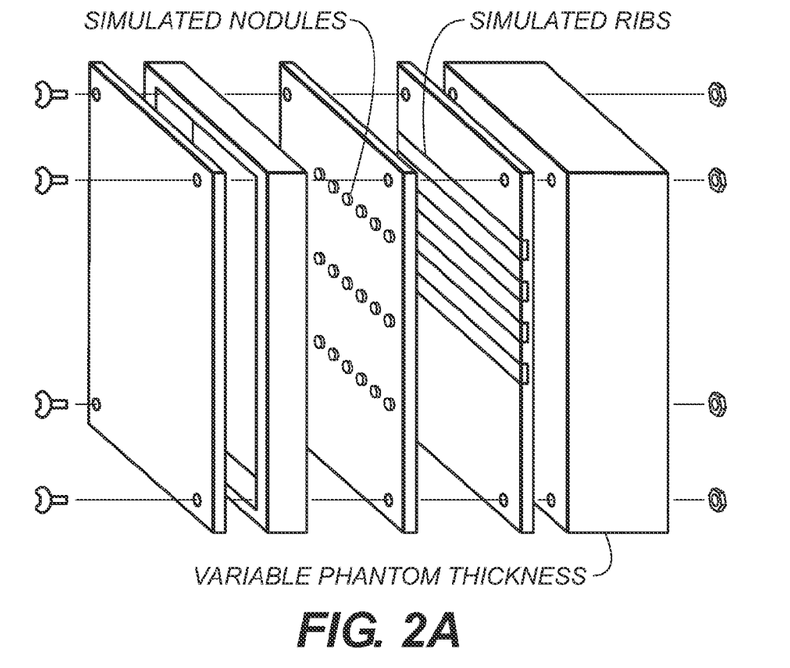
FIG. 2A shows a phantom containing simulated lung nodules and simulated ribs. Chest thickness is variable through the addition or removal of additional acrylic slabs.
Figure 2B:
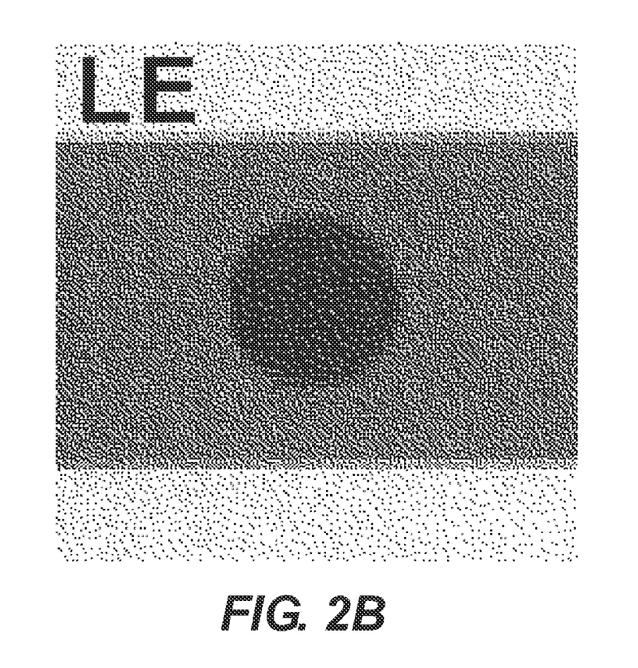
FIGS. 2B-2D show low-energy (LE), high-energy (HE), and dual-energy (DE) images of a simulated lung nodule obscured by a 3 mm rib.
Figure 2C:
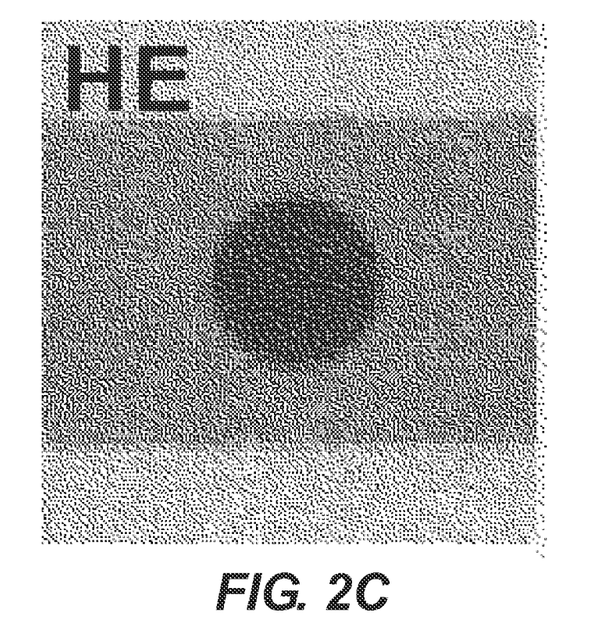
Figure 2D:
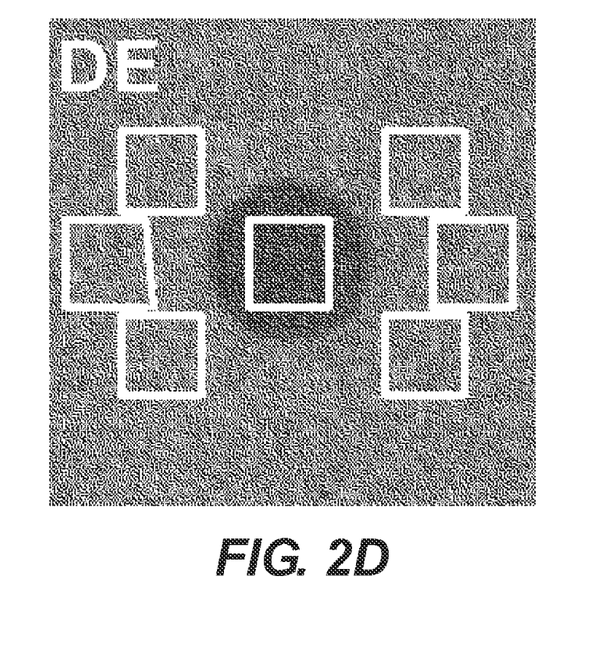

As will be described in more detail below, FIG. 2A shows a "slab" phantom containing simulated lung nodules (9.5 mm diameter right-circular polyethylene cylinders) and simulated ribs (3 and 6 mm thick Al slats). Chest thickness is variable through the addition or removal of additional acrylic slabs. FIGS. 2B-2D show examples of low-energy (LE), high-energy (HE), and dual-energy (DE) images of a simulated lung nodule obscured by a 3 mm rib. ROIs for $SDNR^{DE}$ analysis are shown as rectangles superimposed in FIG. 2D, with six within the background (cancelled bone) and one within the nodule. Regarding the imaging phantom, acquisition techniques, including kVp-pair and dose allocation, were considered using a chest phantom modeled after the ANSI patient-equivalent phantom, as illustrated in FIG. 2A. Lung nodules (9.5 mm right-circular cylinders) were simulated using materials ranging from polyurethane (−500 HU) to nylon (~+75 HU). Ribs were simulated by Al slats (3 and 6 mm thick). The correspondence between phantom thickness and patient thickness was established by measuring the transmitted exposure (i.e., the exposure at the surface of the Bucky grid) for "thin," "average," and "thick" DR technique stations, varying the thickness of acrylic such that the transmitted exposure was ~1 mR in each case. The phantom (acrylic) thicknesses corresponding to "thin" (18 cm), "average" (24 cm), and "thick" (30 cm) patient thicknesses were 7.5, 10, and 12 cm, respectively.

As to the DR technique factors and dose, DR technique factors for "thin," "average," and "thick" patient sizes were obtained from a review of the literature and clinical technique charts. The resulting kVp and mAs are shown in Table I, along with the transmitted exposure measured behind the corresponding thickness of acrylic ($X_{Detector}$) and total imparted energy ($\epsilon^{Total}$).

$A^*_\epsilon$, as indicated by the maximum of the fitted curve. Fits were found to give a better representation of the data under a change of variables, where a modified independent variable, $A'_\epsilon$, was defined as $A'_\epsilon = A_\epsilon/(1-A_\epsilon)$. Nonlinear fitting using the Levenberg-Marquardt method was used to minimize the $\chi^2$-value between fitted data and measurement.

An anthropomorphic chest phantom was imaged as a function of dose allocation ($A_\epsilon$=0.06, 0.30, 0.63, and 0.91) at [70/130] kVp to illustrate the effect of allocation on image quality. As described above, the total dose delivered to the

TABLE I

Summary of DR technique factors for thin, average, and thick patient sizes.

|  | Patient Thickness | | |
| --- | --- | --- | --- |
|  | Thin | Average | Thick |
| $t_{chest}$ | 18 cm | 24 cm | 30 cm |
| $t_{acrylic}$ | 7.5 cm | 10 cm | 12 cm |
| kVp | 120 kVp | 120 kVp | 120 kVp |
| Added Filtration | 1 mm Al + 0.2 mm Cu | 1 mm Al + 0.2 mm Cu | 1 mm Al + 0.2 mm Cu |
| mAs | 2.0 mAs | 3.2 mAs | 6.4 mAs |
| $X_{Detector}$ | (1.10 ± 0.004) mR | (1.14 ± 0.005) mR | (1.34 ± 0.003) mR |
| $\epsilon^{Total}$ | 0.44 µJ/cm² | 0.91 µJ/cm² | 2.08 µJ/cm² |

Dose allocation and kVp pair are now described. Measurements of $SDNR^{DE}$ were performed using the phantom of FIG. 2A across a range of low-kVp (60-90 kVp), high-kVp (120-150 kVp), dose allocation ($A_\epsilon$=~0-1), and patient dose ($\epsilon^{Total}$=0.20-1.73 µJ/cm²). To acquire DE images at various low-kVp, high-kVp, and allocation, but at the same total dose, imparted energies were determined at available kVp and mAs stations permitted by the x-ray generator. For each patient thickness and kVp pair, combinations of $\epsilon^L$(mAs) and $\epsilon^H$(mAs) were identified that yielded a given total dose, $\epsilon^{Total}$, within ±5%. For example, at a kVp-pair of [70/130] kVp, mAs settings of [3.2/16] mAs give $\epsilon^{Total}$=8.80 µJ/cm² with an allocation of $A_\epsilon$=0.29, whereas mAs settings of [10/2] mAs deliver the same total dose, but with allocation of $A_\epsilon$=0.91. In this manner, 10 stations were identified for each patient thickness, kVp pair, and total dose that resulted in allocation in the range $A_\epsilon$~0.1-0.9.

SDNR was evaluated in soft-tissue-only DE images of the phantom, with the bone cancellation parameter determined to minimize the signal difference between regions of simulated rib and background, promoting bone cancellation in the DE soft-tissue images. As illustrated in FIG. 2D, seven ROIs (41×41 pixels) were identified, one within the polyethylene nodule ($I_{nodule}^{DE}$) and six in the adjacent background ($I_{background}^{DE}$). Signal difference, noise, and SDNR were computed as in Eqs. (6), (11), and (14), respectively. The mean and standard deviation in each measurement was determined from ten repeat image acquisitions. Measurements were performed for a total of sixteen kVp-pairs and three phantom thicknesses. In addition, measurements were performed as a function of imparted energy (viz., 11 dose levels ranging from about one-fifth to twice that of a conventional DR chest exam, 0.20-1.73 µJ/cm²) at [70/130] kVp. Slight variations in the dose (constant to within ±5% for fixed patient thickness and kVp-pair) were corrected by normalizing the measured noise by the square Total root of the ratio of calculated and target level of $\epsilon^{Total}$.

Curves of $SDNR^{DE}$ vs. dose allocation (for a given kVp pair and $\epsilon^{Total}$) were fit using a 3-parameter empirical function. Curve fits were intended to guide the reader's eye in the results below and to identify optimal dose allocation, denoted phantom was fixed, and only the dose allocation was varied. The phantom was imaged at techniques corresponding to an average patient, and images on a diagnostic workstation (such as a dual-head, 1536×2048 pixel, 8-bit grayscale displays; AXIS III, National Display Systems, Morgan Hill, Calif.).

Figure 3A:
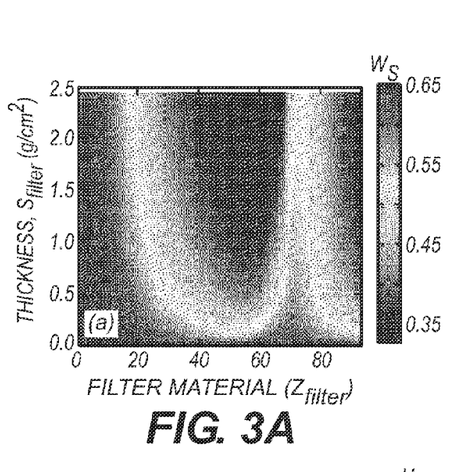
FIGS. 3A-3F shows the effect of added filtration on DE imaging performance.
Figure 3B:
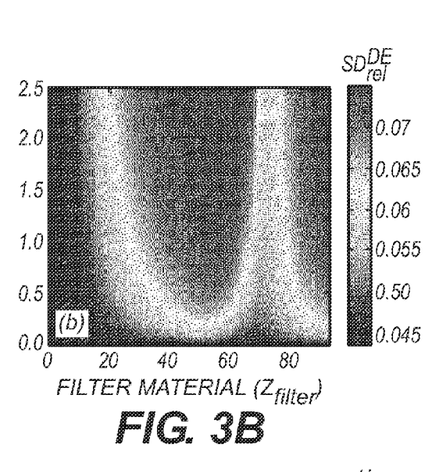
Figure 3C:
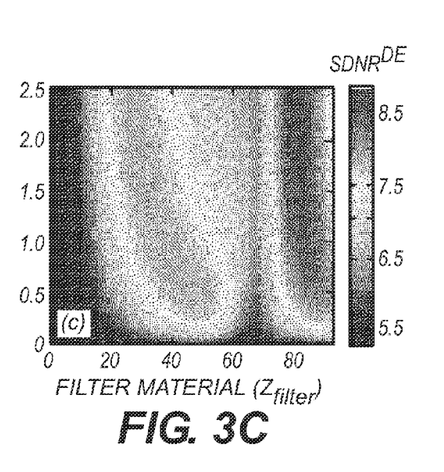
Figure 3D:
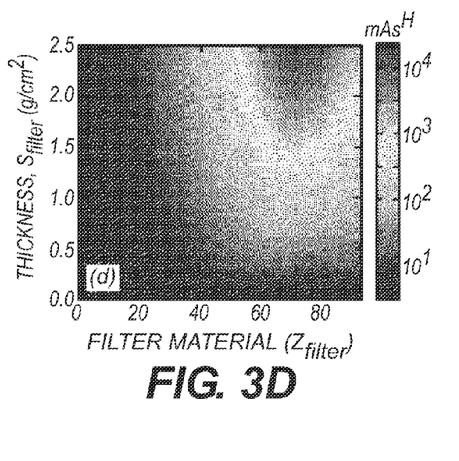
Figure 3E:
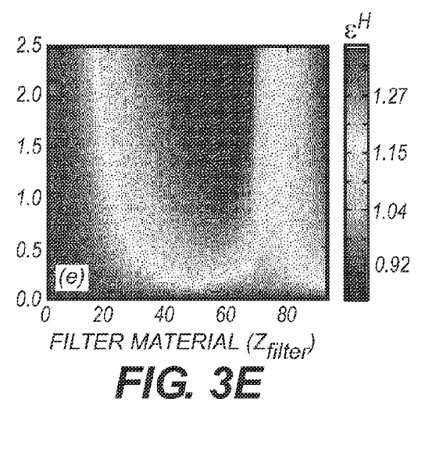
Figure 3F:
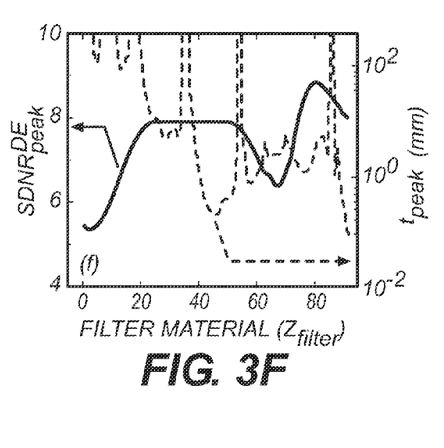

As will be discussed in more detail below, FIGS. 3A-3F shows the effect of added filtration on DE imaging performance. FIGS. 3A-3E are shown as a function of high-kVp filter material ($Z_{filter}$) and thickness ($s_{filter}$). In particular, FIG. 3A shows tissue cancellation parameter, $w_s$, for decomposition of a soft-tissue-only image. FIG. 3B shows DE image signal difference (nodule contrast) computed as in Eqs. (5)-(8). FIG. 3C shows DE image signal-difference to noise ratio, $SDNR^{DE}$. FIG. 3D shows tube mAs required to deliver an exposure of 1 mR to the detector (in the high-kVp projection). Note the logarithmic scale. FIG. 3E shows imparted energy for an average patient thickness. FIG. 3F shows dual-axis plot displaying peak $SDNR^{DE}$ and required filter thickness (converted to mm) as a function of filter material. The plateau in the range $Z_{filter}$~25-50 suggests a range of filters providing nearly equivalent peak $SDNR^{DE}$.

Applicants noted that the dependence of DE imaging parameters and performance metrics on beam filtration, as illustrated in FIGS. 3A-3F. In each case, calculations are shown as a function of high-kVp filter material type ($Z_{filter}$) and thickness ($s_{filter}$), with the low-kVp beam fixed at 70 kVp (+2.5 mm Al added filtration) and at a high-kVp of 130 kVp. FIG. 3(a) shows the reduction in tissue cancellation parameter, $w_s$ ($Z_{filter}$, $s_{filter}$), as filter thickness and atomic number increase (up to $Z_{filter}$~65), corresponding to reduced bone contrast for harder beams. The increase in $w_s$ in the region $Z_{filter}$=65-80 is due to the filter K-edge falling close to the mean energy of the high-kVp beam, effectively softening the beam. A sharp increase occurs as the K-edge increases at higher atomic numbers, $Z_{filter}$>80.

The effect of filtration on $SD^{DE}$ is similar, as shown in FIG. 3B. A harder beam results in increased spectral separation, giving increased DE signal difference at $Z_{filter}$~42-63 and $Z_{filter}$>84 at thicknesses greater than 1.5 g/cm². The K-edge effect at $Z_{filter}$=65-75 reduces $SD^{DE}$ at all thicknesses due to softening of the high-kVp beam. While a harder high-kVp beam increases nodule contrast, the tradeoff in image noise and $SDNR^{DE}$ is illustrated in FIG. 3C, suggesting an optimal filtration in the region Z=25-48 (depending on filter thickness), and a second region of even higher $SDNR^{DE}$ above $Z_{filter}$>77.

The filters thus implied must be considered in relation to tube loading and patient dose, as in FIGS. 3D and 3E. FIG. 3D shows the mAs required to deliver 1 mR to the detector as a function of high-kVp filtration, illustrating the enormous heat load for thick, high-Z filters. Such loading effectively rules out the upper-right quadrant of $(Z_{filter}, s_{filter})$, for which $mAs^H$>~100 mAs. The imparted energy of the high-kVp beam is shown in FIG. 3E, showing increased dose for softer beams and suggesting a region in the range Z ~30-65 consistent with low patient dose.

The peak $SDNR^{DE}$ and the required filter thickness are shown in FIG. 3F. A plateau in $SDNR_{peak}^{DE}$, is seen in the range Z=25-50, indicating a fairly broad range of choices for high-kVp filtration. For filters in the range Z ~45-52, optimal filtration is achieved with filter thickness less than ~1 mm, aiding practical implementation. Reasonable filter selections include ~2.8 mm Cu (Z=29), ~1.2 mm Zr (Z=40), ~0.7 mm Mo (Z=42), ~0.4 mm Pd (Z=46), and ~0.5 mm Ag (Z=47).

Figure 4A:
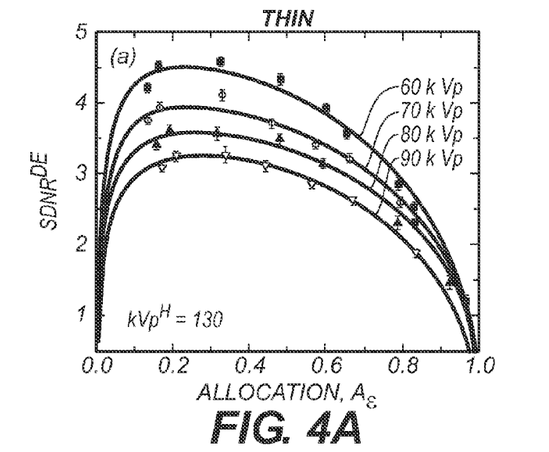
FIGS. 4A-4C show dual-energy SDNR measured as a function of dose allocation for (respectively) thin, average, and thick phantom thicknesses.
Figure 4B:
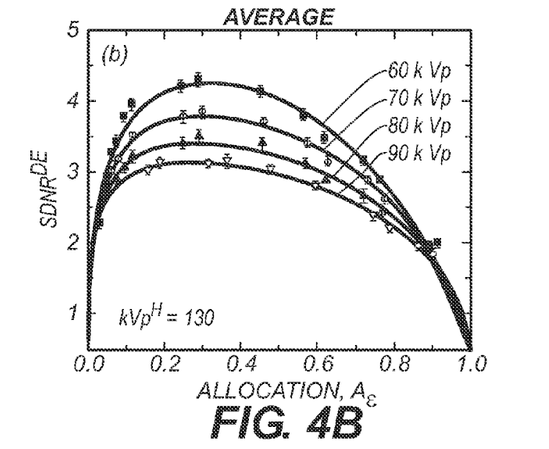
Figure 4C:
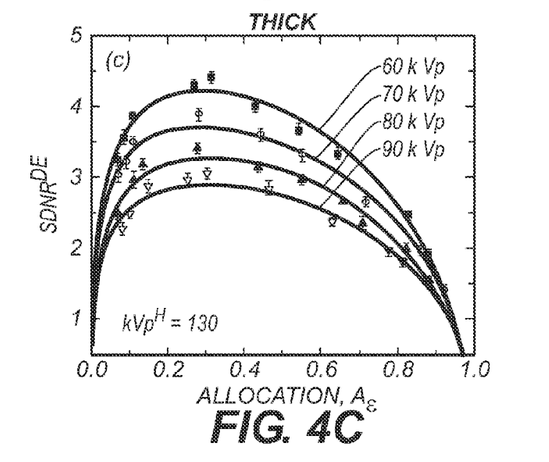

As described in more detail below, FIGS. 4A-4C show dual-energy SDNR measured as a function of dose allocation for thin (FIG. 4A), average (FIG. 4B), and thick (FIG. 4C) phantom thicknesses. The high-kVp was fixed in each case at 130 kVp, with the low-energy technique varied from 60-90 kVp. Curve fits are as described in the text. For each patient thickness, an optimal allocation of $A_\epsilon$~0.3 is suggested.

Figure 5:
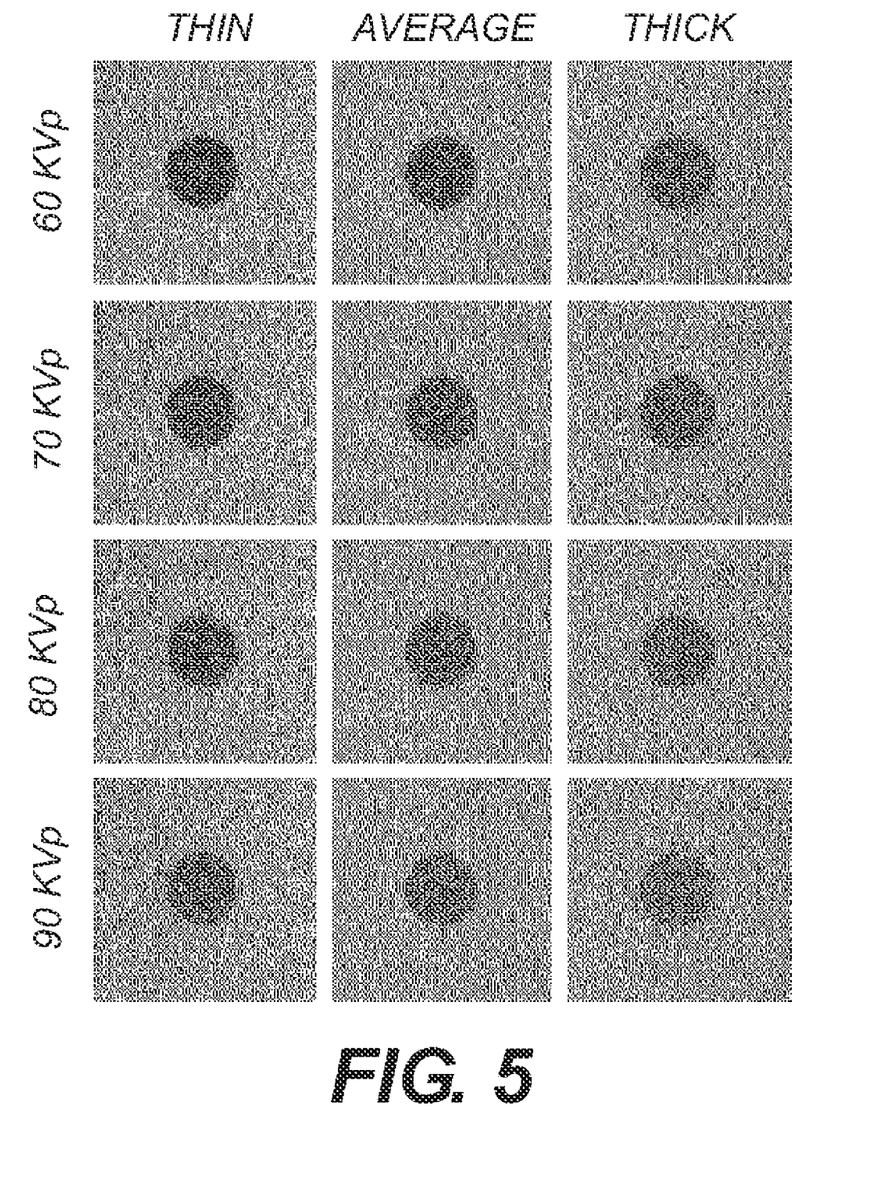
FIG. 5 shows DE soft-tissue images of a polyethylene lung nodule.

For dose allocation and kVp pair, varying the proportion of dose between low- and high-kVp images had an effect on $SDNR^{DE}$. FIGS. 4A-4C show $SDNR^{DE}$ as a function of $A_\epsilon$ at a fixed high-kVp (130 kVp) for three phantom thicknesses. The four curves in each figure correspond to low-kVp of 60, 70, 80, and 90 kVp, respectively, each corresponding to the same total dose level (0.91 µJ/cm$^2$)±5%. For each curve, the peak $SDNR^{DE}$ is found at an allocation of ~0.3, suggesting optimal image quality when one-third of the total dose is imparted by the low-kVp beam. An increase in $SDNR^{DE}$ is observed with increasing spectral separation (i.e., reduced low-kVp). These results are further illustrated in FIG. 5, showing DE images of a simulated (polyethylene) nodule acquired at $A_\epsilon$* for each of the twelve curves shown in FIGS. 4A-4C. For a given phantom thickness, nodule contrast is seen to improve with reduced low-kVp. The reduction in nodule contrast for thicker phantoms is attributed to x-ray scatter, offset somewhat by a reduction in noise (an increase in total dose) such that $SDNR^{DE}$ is similar for each phantom thickness.

More particularly, FIG. 5 shows DE soft-tissue images of a polyethylene lung nodule. Images were acquired at a fixed $kVp^H$=130 and various $kVp^L$ for three phantom thicknesses. Nodule contrast is highest at lower kVp (60 kVp) and for the thin phantom. Reduced contrast and $SDNR^{DE}$ in thicker phantoms is offset in part by an increase in dose (reduced noise).

Measurements as in FIG. 4 were repeated for all sixteen kVp pairs, summarized in FIG. 6, where each parameter plotted corresponds to the peak SDNR (optimal allocation).

Figure 6A:
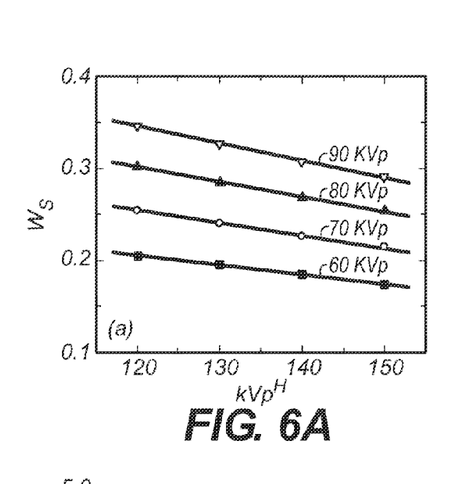
FIGS. 6A-6E show optimal kVp pairs.

More particularly, FIGS. 6A-6E show optimal kVp pairs. FIG. 6A shows tissue cancellation parameter, $w_s$, for optimal bone cancellation. FIGS. 6B-6E show, respectively, relative signal difference (contrast), image noise, peak $SDNR^{DE}$, and optimal dose allocation in the resulting soft-tissue DE images. The results are shown for the average patient thickness.

Figure 6B:
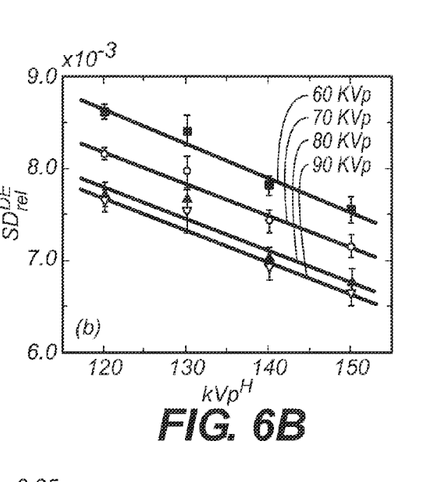
Figure 6C:
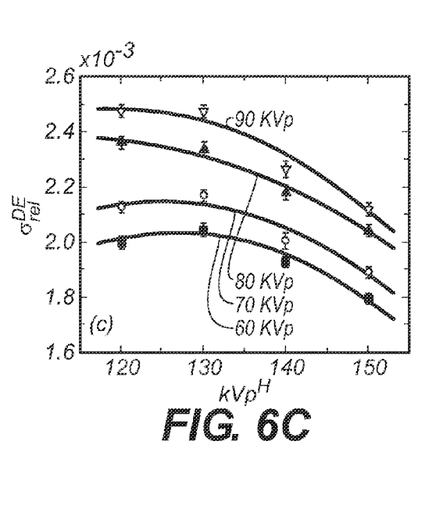
Figure 6D:
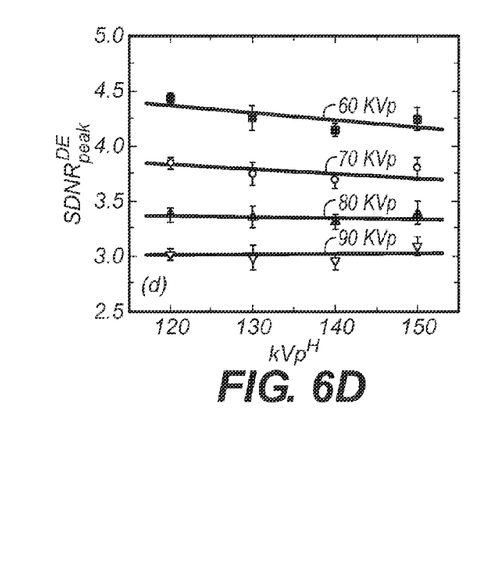

As shown in FIG. 6A, the weighting parameter giving optimal bone cancellation decreases with increasing high-kVp (reduced bone contrast). FIG. 6B illustrates the trend toward lower low-kVp and high-kVp, showing maximum DE soft-tissue signal difference at [60/120] kVp. The results suggest a tradeoff between spectral separation (i.e., increased contrast for lower low-kVp) and x-ray scatter (i.e., reduced nodule contrast at higher high-kVp). As shown in FIG. 6C, image noise was highest at 90 kVp because of decreased quantum detection efficiency (QDE). Taken together, the effects of kVp selection on nodule contrast and noise are shown in FIG. 6D, where $SDNR^{DE}$ is found to be highest at [60/120] kVp, reduces sharply with increasing low-kVp (reduced spectral separation), and reduces slightly with increasing high-kVp (increased x-ray scatter).

Figure 6E:
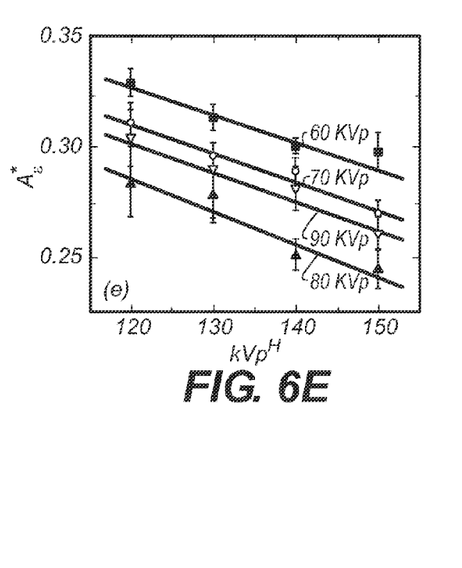

As shown in FIG. 6E, the selection of kVp-pair was found to have a small effect on the optimal dose allocation, with $A_\epsilon$~0.3 presenting a fairly smooth optimum across all conditions. Although the trends are comparable to the experimental error, higher allocation was required for reduced low- and high-kVp, suggesting: i) adequate transmission through the patient required a larger proportion of dose at the lower low-kVp; and ii) increasing the high-kVp necessitates lower allocation to reduce quantum noise associated with reduced QDE at higher kVp. An inflection is observed between low-kVp of 80 and 90 kVp, indicating a tradeoff between imparted energy, transmitted exposure, and quantum noise. In particular, the increased noise at 90 kVp combined with the larger weighting parameter suggest an increase in the dose allocation.

Figure 7A:
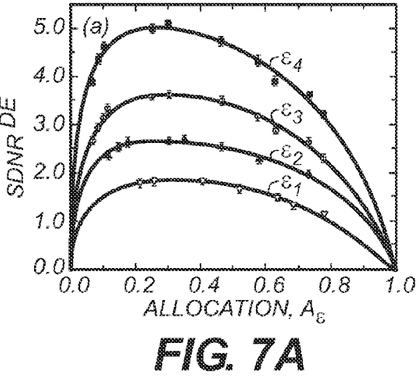
FIGS. 7A-7D show the effect of dose on DE imaging performance.
Figure 7B:
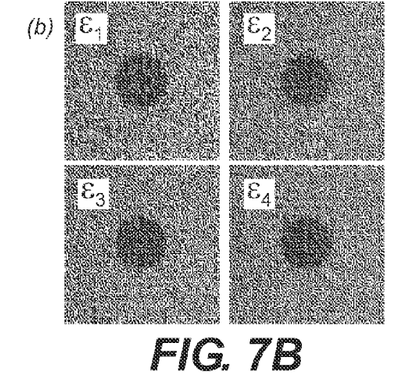
Figure 7C:
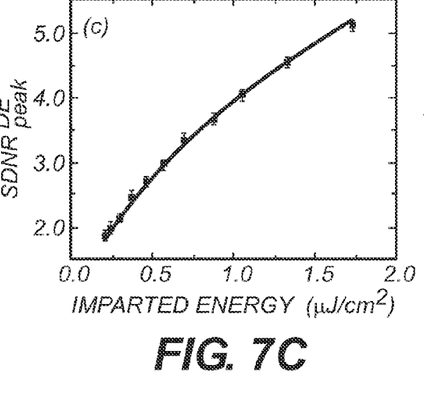
Figure 7D:
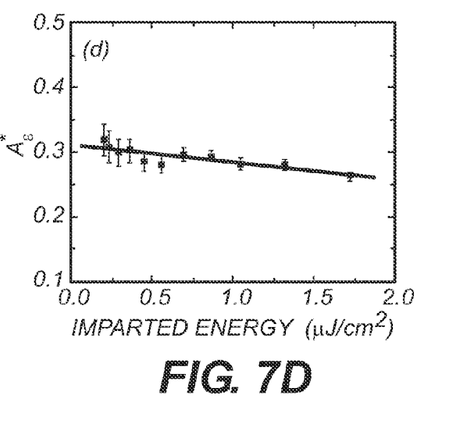

FIGS. 7A-7D show the effect of dose on DE imaging performance. More particularly, FIG. 7A shows DE image SDNR measured as a function of dose allocation for four total dose levels ($\epsilon_1$=0.203, $\epsilon_2$=0.453, $\epsilon_3$=0.864, and $\epsilon_4$=1.725 µJ/cm$^2$). FIG. 7B shows DE images of a polyethylene nodule acquired at conditions corresponding to $SDNR_{peak}^{DE}$ for $\epsilon_1$, $\epsilon_2$, $\epsilon_3$, and $\epsilon_4$. FIG. 7C shows Peak $SDNR^{DE}$ as a function of total imparted energy, plotted in comparison to a square-root fit. FIG. 7D shows optimal dose allocation measured as a function of total imparted energy, with a linear fit superimposed and suggesting a slight decrease with higher total dose. The results were acquired at [70/130] kVp.

Still referring to FIGS. 7A-7D, for dose allocation and total dose, for a fixed kVp-pair and patient thickness, the behavior of $w_s$, $SD^{DE}$, $\sigma^{DE}$, $SDNR^{DE}$, peak $SDNR^{DE}$, and optimal dose allocation was investigated as a function of the total imparted energy. $SDNR^{DE}$ vs. $A_\epsilon$ for imparted energy ranging from approximately one-fifth to double that of a conventional DR radiograph are shown in FIG. 7A. DE images of the polyethylene nodule acquired at optimal allocation are shown in FIG. 7B. The tissue-weighting parameter and signal difference did not appreciably vary with dose, although image noise decreased in proportion to the inverse square-root of dose as expected, resulting in the square-root dependence in SDNR k shown in FIG. 7C. Reduction of or $\sigma_{rel}^{DE}$ was the driving factor for the increase of peak $SDNR^{DE}$. The optimal dose allocation decreased slightly with dose as shown in FIG. 7D.

Referring now to Table II, a dual-energy technique chart, the optimal DE imaging techniques described above a relevant to a technique chart for use of the DE imaging prototype in patient studies, including optimal filtration, kVp, and mAs for low- and high-kVp projections as well as dose allocation. Table II summarizes the optimal techniques along with energy imparted and entrance surface dose for three patient thicknesses.

TABLE II

Dual-energy technique chart describing optimal acquisition techniques for three patient thicknesses.

| | Patient Thickness | | | | | | | | |
|---|---|---|---|---|---|---|---|---|---|
| | Thin (18 cm chest) | | | Average (24 cm chest) | | | Thick (30 cm chest) | | |
| | Low | High | Total | Low | High | Total | Low | High | Total |
| kVp | 60 | 120 | — | 60 | 120 | — | 60 | 120 | — |
| mAs | 3.2 | 16 | — | 5 | 25 | — | 10 | 50 | — |
| $\epsilon$ ($\mu$J/cm$^2$) | 0.131 | 0.298 | 0.429 | 0.246 | 0.641 | 0.887 | 0.543 | 1.539 | 2.082 |
| ESD (mGy) | 0.032 | 0.040 | 0.072 | 0.052 | 0.065 | 0.117 | 0.106 | 0.132 | 0.238 |
| $A_\epsilon^*$ | — | — | 0.31 | — | — | 0.28 | — | — | 0.26 |

Figure 8:
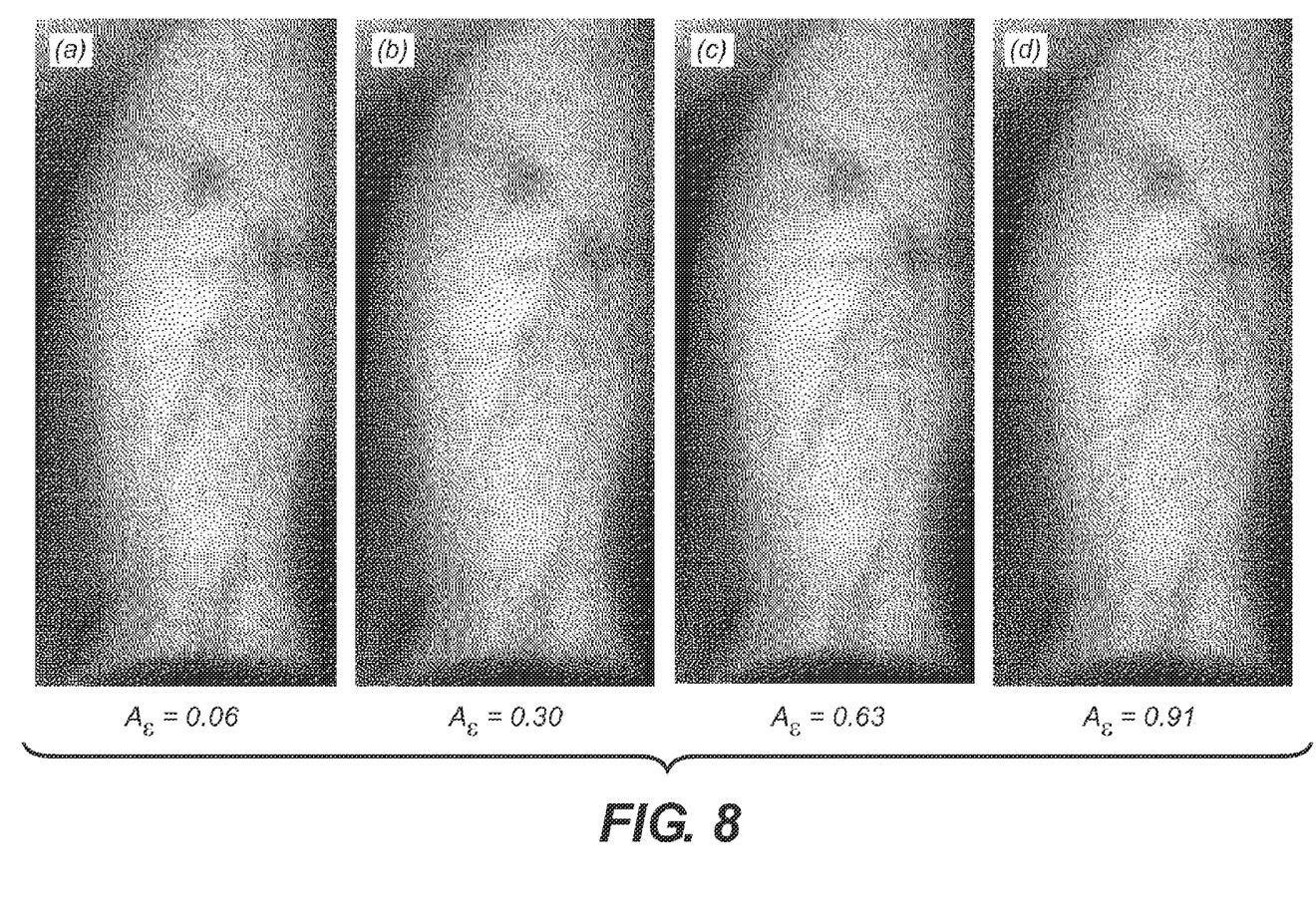
FIG. 8 shows the effect of dose allocation on dual energy imaging performance.

An anthropomorphic phantom is not described with reference to FIG. 8. FIG. 8 illustrates the effect of dose allocation on DE imaging performance. More particularly, FIG. 8 shows DE soft-tissue images of an anthropomorphic phantom acquired at four levels of dose allocation. Images were acquired at [70/130] kVp and at equivalent total dose (~0.9 $\mu$J/cm$^2$, corresponding to the energy imparted for an average patient). Optimal image quality is obtained at $A_\epsilon$=0.30. A noticeable increase in image noise is evident at very low ($A_\epsilon$=0.06) and very high ($A_\epsilon$=0.91) allocation. In each case, a magnified view of the right lung of an anthropomorphic phantom is shown for DE soft-tissue images acquired across a broad range in dose allocation. The results are generally consistent with FIG. 4B, indicating strong degradation in image quality at extreme values of allocation (e.g., $A_\epsilon$=0.06 and $A_\epsilon$=0.91), with a fairly weak dependence in the range $A_\epsilon$~0.2-0.6. Interpretation by an expert radiologist indicates that the visibility of spherical nodules in the lung is highest at $A_\epsilon$=0.30, slightly reduced at $A_\epsilon$=0.63, and significantly degraded at allocation extremes.

As such, it is noted that DE imaging can reduce the contribution of anatomical clutter within a chest radiograph, which has recently shown to be a significant impediment in the visualization of soft-tissue structures. To promote maximum DE image quality, careful consideration of tradeoffs in soft-tissue contrast and image noise is taken into account. Applicants describe DE imaging techniques that promote soft-tissue visibility in DE soft-tissue images, specifically in the context of chest imaging. The results pertain to DE image decomposition by log-weighted subtraction, with future work to include optimization in association with various post-processing techniques (e.g., noise reduction) and alternative imaging tasks (e.g., visualization of bony detail in the bone-only image).

There is noted the role of differential filtration between low- and high-kVp beams, showing that strong filtering of the high-kVp beam is relevant to technique optimization. The present invention is consistent with these findings, demonstrating further the tradeoffs between increased spectral separation (improved nodule contrast) and image noise. Optimal filter material types and thickness emerge that balance the tradeoffs between contrast and noise, presenting techniques that are achievable without undue tube loading or patient dose. A range of high-kVp filters providing comparable imaging performance is suggested—e.g., as shown in FIG. 3, metals in the range $Z_{filter}$~40-47 with thickness less than 1 mm.

The optimal kVp pair in DE imaging has been shown to be task dependent with selections ranging from [60/120] to [80/110] kVp. The results above indicate an optimal soft-tissue imaging performance at a kVp pair of [60/120] kVp for all patient thicknesses investigated and with total dose equivalent to that of a single chest radiograph. Low-kVp exhibited a stronger effect on SDNR$^{DE}$, with 60 kVp providing improved nodule contrast and higher detector efficiency. The effect of high-kVp was less significant, suggesting competing effects among energy separation (contrast), image noise, and x-ray scatter in relation to soft-tissue visibility. The optimal dose allocation for this imaging task was also shown to be fairly constant ($A^*_\epsilon$~0.3) for all patient thicknesses investigated. The majority of patient dose is allotted to the high-kVp image to reduce noise associated with the high-kVp image.

Conventionally, DE imaging has been somewhat constrained by the need for increased total imaging dose, but the optimal techniques described above corresponds to a total dose equivalent to that of a single chest radiograph. This will facilitate deployment of DE imaging systems at clinically accepted dose levels. In addition, the insensitivity of certain optima (e.g., kVp pair and dose allocation) to patient thickness is desirable from the standpoint of simplified system implementation—i.e., once the optima are established, they are valid for a broad range of patient body types.

In the following description, a preferred embodiment of the present invention will be described as a software program. Those skilled in the art will recognize that the equivalent of such software may also be constructed in hardware. Because image manipulation algorithms and systems are well known, the present description will be directed in particular to algorithms and systems forming part of, or cooperating more directly with, the method in accordance with the present invention. Other aspects of such algorithms and systems, and hardware and/or software for producing and otherwise processing the image signals involved therewith, not specifically shown or described herein may be selected from such systems, algorithms, components and elements known in the art.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. An x-ray imaging system for generating dual energy x-ray images comprising:
an x-ray source;
an image detector spaced from the x-ray source to accommodate a subject to be imaged, the x-ray source being selectively switchable between first and second different x-ray energy levels, the first x-ray energy level being selected within a range of approximately 50-70 kVp and the second x-ray energy level being selected within a range of approximately 110-130 kVp, with a dose allocation, for the first x-ray energy level, being selected within a range of approximately 30-40 percent of a total dose of the first x-ray energy level and the second x-ray energy level;
a filter, for the second x-ray energy level, disposed between the x-ray source and the subject, the filter being selected of a filter material range $Z_{filter}$ of approximately 40-47 and a thickness of less than approximately 1 mm; and
a computer controlling the x-ray source to irradiate the subject with the first and second energy levels to generate first and second x-ray images.

2. The x-ray imaging system of claim 1, wherein:
the first x-ray energy level is approximately 60 kVp;
the second x-ray energy level is approximately 120 kVp;
the dose allocation is approximately 30 percent; and
the filter having a filter material $Z_{filter}$ of approximately 47 and a thickness of approximately 0.4-0.5 mm.

3. A method acquiring dual energy x-ray images comprising:
providing a computer to control acquisition of first and second x-ray images of a subject using an x-ray detector and an x-ray source to irradiate a subject;
positioning at least one filter between the x-ray source and the subject during the acquisition of the first and second x-ray images of the subject, the at least one filter comprising a filter, for the second x-ray image, being selected of a filter material range $Z_{filter}$ of approximately 40-47 and a thickness of less than approximately 1 mm;
obtaining the first x-ray image of the subject generated at a first energy level, the first energy level being selected within a range of approximately 50-70 kVp; and
obtaining the second x-ray image of the subject generated at a second energy level, the second energy level being selected within a range of approximately 110-130 kVp, with a dose allocation, for the first energy level, being selected within a range of approximately 30-40 percent of a total dose of the first energy level and the second energy level.

4. The method of claim 3, wherein:
the first x-ray energy level is approximately 60 kVp;
the second x-ray energy level is approximately 120 kVp;
the dose allocation is approximately 30 percent; and
the filter having a filter material $Z_{filter}$ of approximately 47 and a thickness of approximately 0.4-0.5 mm.

* * * * *